(12) United States Patent
Yoneda et al.

(10) Patent No.: US 8,154,683 B2
(45) Date of Patent: Apr. 10, 2012

(54) ILLUMINATION DEVICE AND METHOD FOR MANUFACTURING THE SAME

(75) Inventors: Kenji Yoneda, Kyoto (JP); Kenji Miura, Kyoto (JP)

(73) Assignee: CCS Inc., Kyoto-shi (JP)

( * ) Notice: Subject to any disclaimer, the term of this patent is extended or adjusted under 35 U.S.C. 154(b) by 0 days.

(21) Appl. No.: 13/130,530

(22) PCT Filed: Nov. 26, 2009

(86) PCT No.: PCT/JP2009/069900
§ 371 (c)(1),
(2), (4) Date: May 2, 2011

(87) PCT Pub. No.: WO2010/061868
PCT Pub. Date: Jun. 3, 2010

(65) Prior Publication Data
US 2011/0220958 A1    Sep. 15, 2011

(30) Foreign Application Priority Data
Nov. 26, 2008 (JP) ................................. 2008-301532

(51) Int. Cl.
*G02F 1/1335* (2006.01)

(52) U.S. Cl. ................. 349/61; 349/49; 349/50; 349/56; 349/58; 257/79; 257/98; 257/99

(58) Field of Classification Search ..................... 349/49, 349/50, 56, 58, 61; 257/79, 98, 99
See application file for complete search history.

(56) References Cited

U.S. PATENT DOCUMENTS

| | | | |
|---|---|---|---|
| 7,924,371 B1* | 4/2011 | Davis | 349/68 |
| 7,968,901 B2* | 6/2011 | Yamashita et al. | 257/99 |
| 2004/0070963 A1* | 4/2004 | Miwa | 362/26 |

FOREIGN PATENT DOCUMENTS

| JP | 2975893 B2 | 11/1999 |
|---|---|---|
| JP | 2008078066 A | 4/2008 |

OTHER PUBLICATIONS

ISA Japanese Patent Office, International Search Report of PCT/JP2009/069900, Mar. 16, 2010, 1 page.

* cited by examiner

*Primary Examiner* — Jennifer Doan
(74) *Attorney, Agent, or Firm* — Alleman Hall McCoy Russell & Tuttle LLP (57) ABSTRACT

The present invention relates to a method for easily manufacturing an illumination device in which a surface mount chip-type LED is used, and a wiring board is formed into a truncated conical or another shape. The method includes, in a flexible strip-like wiring board having a partial ring or a linear shape, providing a through-hole T for filling with solder paste S at a wiring end portion L to be connected with a terminal of an LED, temporarily fixing the LED with bond B onto the wiring board held in a plate-like state, filling the through-hole T with the solder paste S from a back surface of the wiring board, rounding the wiring board mounted with the LED into a truncated conical or cylindrical shape, and reflowing the wiring board in the rounded state to solder the LED.

8 Claims, 6 Drawing Sheets

ILLUMINATION DEVICE AND METHOD FOR MANUFACTURING THE SAME

TECHNICAL FIELD

The present invention relates to an illumination device in which an LED element is mounted on a flexible strip-like wiring board having a partial ring shape or a linear shape, and the wiring board is rounded and formed into a truncated conical shape or a cylindrical shape with end edges of the wiring board being brought into abutting contact with each other, and a method for manufacturing the illumination device.

Background Art

This sort of illumination device was first developed by the present inventor (see Patent literature 1), and conventionally configured in such a manner that, into a through-hole provided in a flexible wiring board having the above-described shape, a lead terminal of a shell-type LED is inserted and soldered, and then the wiring board is rounded and formed into a truncated conical shape or a cylindrical shape with end edges of the wiring board being brought into abutting contact with each other, or the wiring board is first rounded, and then the lead terminal of the shell-type LED is inserted into the through hole and soldered.

CITATION LIST

Patent Literature

Patent literature 1: Japanese Patent No. 2,975,893

SUMMARY OF INVENTION

Technical Problem

However, in recent years, for various reasons, in place of the shell-type LED, a chip-type LED of a surface mount type has been becoming mainstream, and if such a chip-type LED is soldered onto the flexible wiring board as before, there occurs a problem that the flexible wiring board cannot be bent due to fixing force of the solder, and therefore cannot be formed into the truncated conical shape or another shape.

On the other hand, if for this reason, the flexible board is first bent, it becomes very difficult to solder the chip-type LED of a surface mount type onto the board. The chip-type LED of a surface mount type is essentially based on the assumption that the LED is flatly placed on a board that is applied with solder paste and in a plate-like state, and under the condition that the LED is not shifted from a predetermined position by a viscous property of the solder paste, the solder paste is reflowed to thereby solder the LED. That is, if the board is first bent, at least the viscous property of the solder paste cannot prevent the chip-type LED from being removed from the solder paste due to the bend of the board, and therefore cannot fix the LED at the predetermined position, resulting in the shift or the like of the LED, so that it becomes very difficult to perform the soldering.

The present invention is made in consideration of the above problems, and has a main desired object to provide an illumination device in which, although a chip-type LED of a surface mount type is used, a wiring board is formed into a truncated conical shape or another shape, and a method is provided for easily manufacturing the illumination device.

Solution to Problem

In summary, an illumination device according to the present invention is adapted on the basis of a completely new idea that a through-hole conventionally used to pass a lead terminal through is used for filling with solder paste from a board back surface, and has a new configuration in which although a chip-type LED of a surface mount type is mounted, a through-hole is provided on a board side.

That is, a method for manufacturing an illumination device according to the present invention is a method for manufacturing an illumination device in which a chip-type LED is mounted on a surface of a flexible strip-like wiring board having a partial ring shape or a linear shape, and the wiring board is rounded and formed into a truncated conical shape or a cylindrical shape with end edges of the wiring board being brought into abutting contact with each other, the method having: a through-hole forming step of, in the wiring board, providing a through-hole for filling with solder paste at a wiring end portion to be connected with a terminal of the LED; a mounting step of temporarily fixing the LED with bond onto the wiring board in a plate-like state, and filling the through-hole with the solder paste from a back surface of the wiring board; a rounding step of rounding the wiring board into the shape, the wiring board being mounted with the LED in the mounting step and having the through hole filled with the solder paste; and a soldering step of reflowing the wiring board in a rounded state.

Also, an illumination device according to the present invention is an illumination device in which a chip-type LED is mounted on a surface of a flexible strip-like wiring board having a partial ring shape or a linear shape, and the wiring board is rounded and formed into a truncated conical shape or a cylindrical shape with end edges of the wiring board being brought into abutting contact with each other, the illumination device being formed by: in the wiring board, providing a through-hole for filling with solder paste at a wiring end portion to be connected with a terminal of the LED; temporarily fixing the LED with bond onto the wiring board held in a plate-like state, and filling the through-hole with the solder paste from a back surface of the wiring board; and rounding the wiring board into the shape, the wiring board being mounted with the LED and having the through hole filled with the solder paste, and reflowing the wiring board in the rounded state to solder the LED.

If so, the LED is temporarily fixed with the bond onto the wiring board in the plate-like state, and also the through hole is filled with the solder paste from the back surface of the wring board, so that even if the wiring board is rounded, the terminal of the LED can be prevented from being displaced from the wiring end portion of the wiring board, and the through hole can be filled with solder paste sufficient to make an electrical connection between the terminal of the LED and the wiring end portion of the wiring board on the surface of the wiring board. Further, in the plate-like state, the LED is not completely fixed onto the wiring board by soldering but only temporarily fixed with the bond, so that the wiring board can be easily rounded into the truncated conical shape or cylindrical shape from the plate-like state, and then by performing the reflow, a plurality of LEDs arranged at desired positions on a curved surface of the shape can be soldered at once.

Also, in the method for manufacturing an illumination device in which a chip-type LED of a surface mount type is soldered onto a wiring board rounded into a truncated conical shape or a cylindrical shape, as another aspect in which the LED is temporarily fixed with bond onto the wiring board, a method for manufacturing an illumination device in which a chip-type LED is mounted on a flexible strip-like wiring board having a partial ring shape or a linear shape, and the wiring board is rounded and formed into a truncated conical shape or a cylindrical shape with end edges of the wiring board being brought into abutting contact with each other may have: a through-hole forming step of, in the wiring board, providing a through-hole for filling with solder paste at a wiring end portion to be connected with a terminal of the LED; a temporary fixing step of temporarily fixing the LED with bond onto a surface of the wiring board in a plate-like state; a rounding step of rounding the wiring board into the shape, the wiring board being mounted on the surface with the LED by the temporary fixing step; a filling step of filling the through hole with the solder paste from a back surface of the wiring board in a rounded state; and a soldering step of reflowing the wiring board in the rounded state, the wiring board having the through-hole filled with the solder paste.

As a method for manufacturing an illumination device in which only a part of a chip-type LED is soldered to a wiring end portion of a wiring board to temporarily fix the LED onto the wiring board, and thereby the wiring board can be rounded into a truncated conical shape or a cylindrical shape, there is cited a method for manufacturing an illumination device in which a chip-type LED is mounted on a surface of a flexible strip-like wiring board having a partial ring shape or a linear shape, and the wiring board is rounded and formed into a truncated conical shape or a cylindrical shape with end edges of the wiring board being brought into abutting contact with each other, the method having: a through-hole forming step of, in the wiring board, providing a through-hole for filling solder paste at a part of a wiring end portion to be connected with a terminal of the LED; a mounting step of bringing the wiring board into a plate-like state, soldering with first solder a wiring end portion other than the wiring end portion where the through-hole for filling the solder paste is formed and a terminal of the LED to each other, and filling the through-hole with paste-like second solder that is melted at a lower temperature than that of the first solder; a rounding step of rounding the wiring board into the shape, the wiring board being mounted with the LED in the mounting step and having the through-hole filled with the paste-like second solder; and a soldering step of reflowing the wiring board in a rounded state at a temperature at which the first solder is not melted but the second solder is melted.

Also, as a specific aspect of an illumination device manufactured by any of the manufacturing methods described in the previous paragraphs, there is cited an illumination device in which a chip-type LED is mounted on a surface of a flexible strip-like wiring board having a partial ring shape or a linear shape, and the wiring board is rounded and formed into a truncated conical shape or a cylindrical shape with end edges of the wiring board being brought into abutting contact with each other, the illumination device being formed by: in the wiring board, providing a through-hole for filling solder paste at a part of a wiring end portion to be connected with a terminal of the LED; bringing the wiring board into a plate-like state, soldering with first solder a wiring end portion other than the wiring end portion where the through-hole for filling the solder paste is formed and a terminal of the LED to each other, and filling the through-hole with paste-like second solder that is melted at a lower temperature than that of the first solder; and rounding the wiring board into the shape, the wiring board being mounted with the LED in the mounting step and having the through-hole filled with the paste-like second solder, and reflowing the wiring board in a rounded state at a temperature at which the first solder is not melted but the second solder is melted.

As the method for manufacturing an illumination device in which only a part of a chip-type LED is soldered to a wiring end portion of a wiring board to temporarily fix the LED onto the wiring board, and thereby the wiring board can be rounded into a truncated conical shape or a cylindrical shape, a method for manufacturing an illumination device in which a chip-type LED is mounted on a surface of a flexible strip-like wiring board having a partial ring shape or a linear shape, and the wiring board is rounded into a truncated conical shape or a cylindrical shape with end edges of the wiring board being brought into abutting contact with each other may have: a through-hole forming step of, in the wiring board, providing a through-hole for filling solder paste at a part of a wiring end portion to be connected with a terminal of the LED; a mounting step of bringing the wiring board into a plate-like state, soldering with first solder a wiring end portion other than the wiring end portion where the through-hole for filling the solder paste is formed and a terminal of the LED to each other, and filling the through-hole with paste-like second solder; a rounding step of rounding the wiring board into the shape, the wiring board being mounted with the LED in the mounting step and having the through-hole filled with the paste-like second solder; and a soldering step of, in the wiring board in a rounded state, providing heat from a back surface of the through-hole to melt the second solder.

To more efficiently perform soldering with the first solder and improve workability, in the mounting step, it is only necessary to use paste-like first solder to perform soldering by reflow.

Advantageous Effects of Invention

According to the method for manufacturing an illumination device and the illumination device configured as described above according to the present invention, the through-hole conventionally used to pass a lead terminal through is used to fill the solder paste from the board back surface, so that the trouble that an LED is completely fixed onto a wiring board in a plate-like state to thereby fail to round the wiring board can be prevented, and the wiring board can be easily formed into a truncated conical shape or another shape to manufacture the illumination device.

BRIEF DESCRIPTION OF DRAWINGS

FIG. 5(a)-5(e) are schematic diagrams illustrating a flow of a manufacturing method according to a first embodiment; and FIG. 6(a)-6(e) are schematic diagrams illustrating a flow of a manufacturing method according to a second embodiment.

DESCRIPTION OF EMBODIMENTS

A first embodiment of the present invention is described below referring to the drawings. In a perspective view of FIG. 1, an illumination device 100 manufactured with use of a manufacturing method of the present embodiment is illustrated. The illumination device 100 is, as illustrated in FIG. 1, configured such that chip-type LEDs 1 of a surface mount type are soldered onto a flexible printed wiring board 2 such as a flexible board; and the printed wiring board 2 is rounded into a truncated conical shape so as to arrange the LEDs inside, and attached inside a substantially cylindrically shaped illumination case 3 of which one end is opened.

Figure 1:
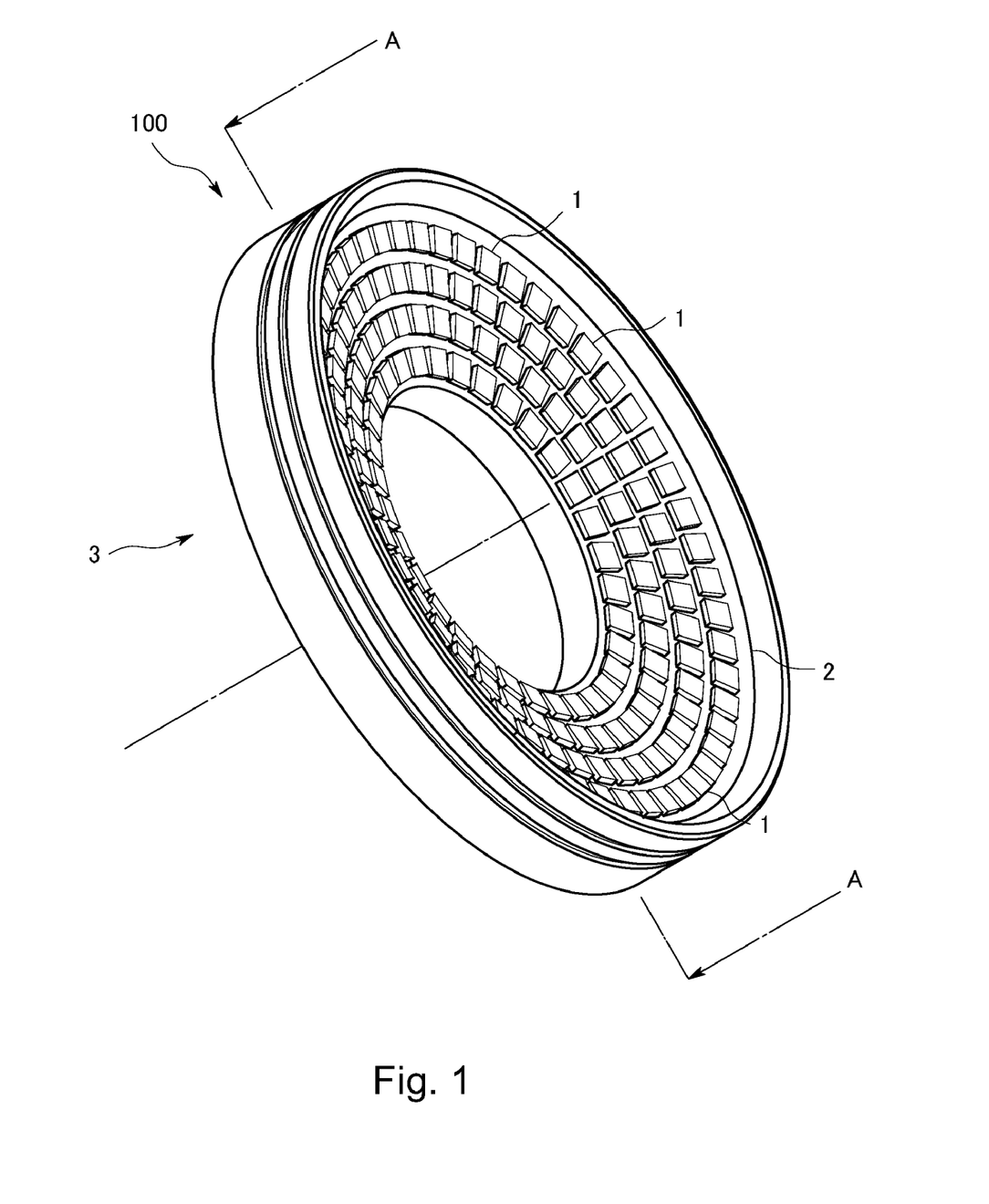
FIG. 1 is a schematic perspective view of an illumination device manufactured with use of a manufacturing method of the present invention.
Figure 2:
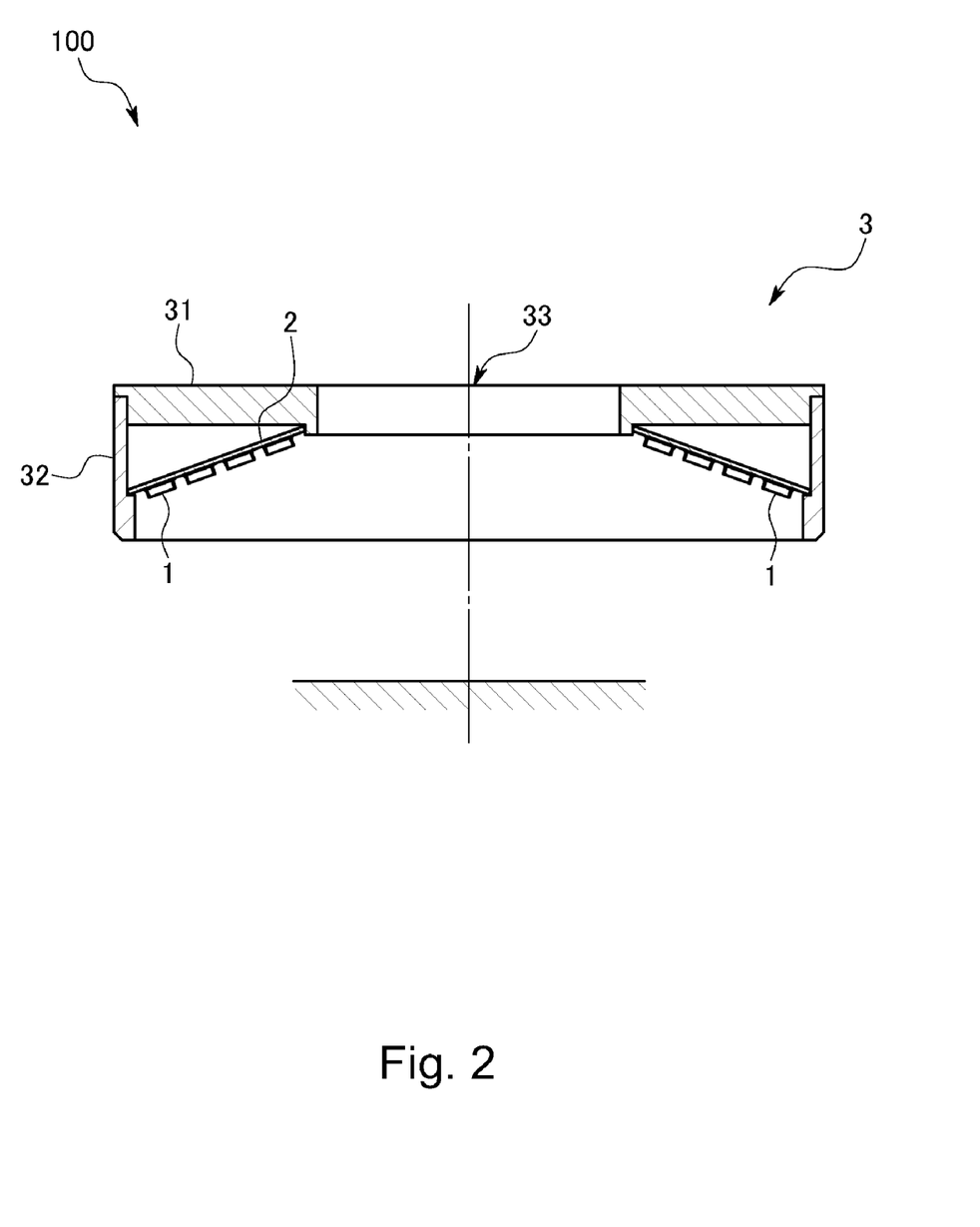
FIG. 2 is a diagram of an A-A cross section in FIG. 1.

The illumination case 3 is, as illustrated in FIG. 2 that is a diagram of an A-A cross section in FIG. 1, configured to include: a lid member 31 having a through-hole 33 in the center serving as an upper surface of the illumination case 3; and a holding body 32 that is attached to the lid member 31, serves as a side surface of the illumination case 3; and holds the printed wiring board 2 along with the lid member. The through-hole 33 is one that is, for example, in the case of using the illumination device 100 for illumination for inspection, used to view or photograph an inspection object.

Figure 3:
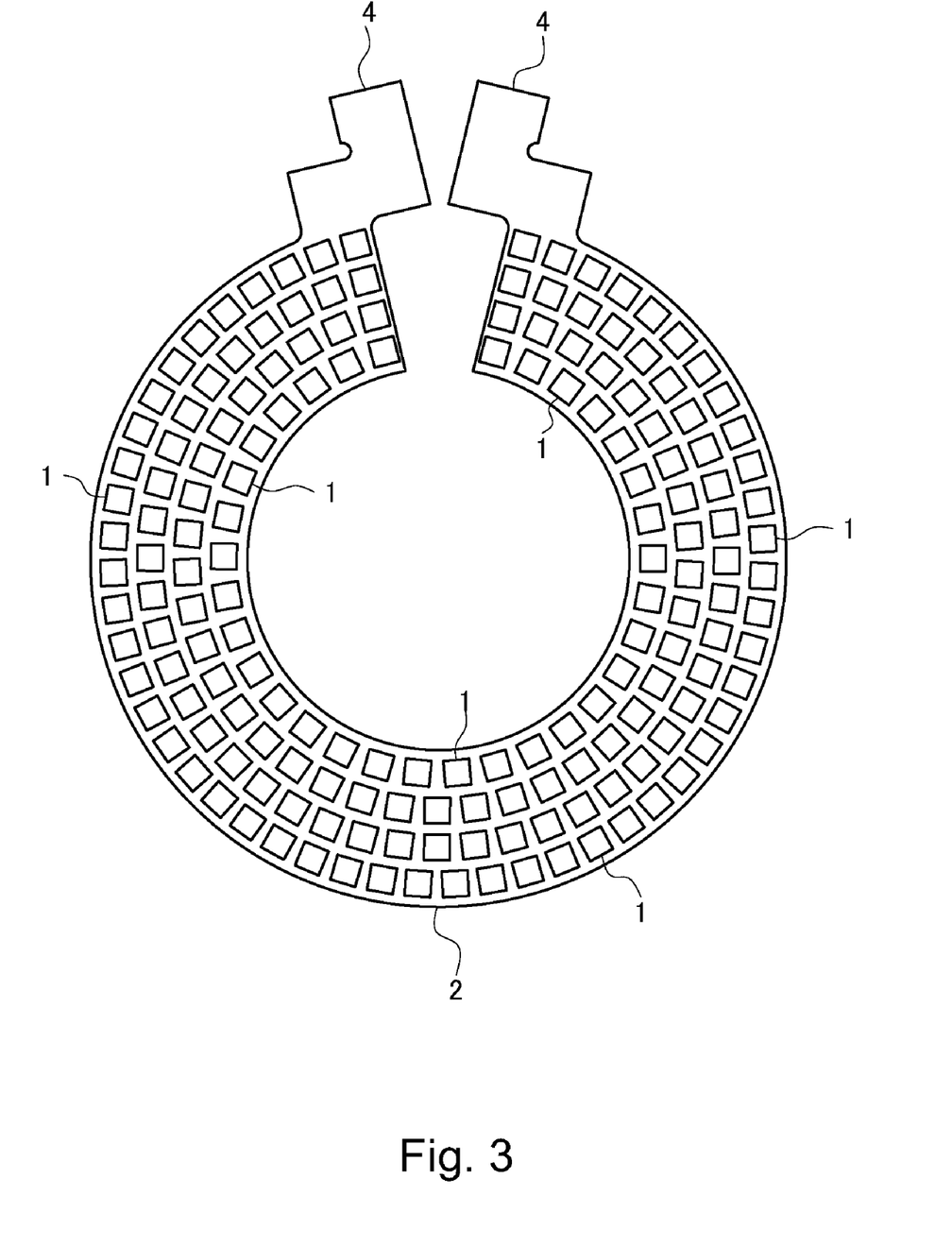
FIG. 3 is a schematic plan view illustrating a plate-like state of a wiring board used for the illumination device.

The printed wiring board 2 is, as illustrated in FIG. 3, one having a partial ring shape partially having a cutout, and onto a surface thereof, the plurality of chip-type LEDs 1 of a surface mount type are attached by soldering. Further, the printed wiring board 2 is provided, at both end portions of the cutout, with a pair of grapple members 4 that are intended to, when the printed wiring board 2 is rounded into the truncated conical shape with end edges of the printed wiring board 2 being brought into abutting contact with each other, keep the shape. The pair of grapple members 4 may be, after bonding by another method such as using a bond at the time of assembling of the illumination device 100, cut off or left as is.

Typically, when the chip-type LEDs 1 of a surface mount type are attached, such a printed wiring board 2 is not provided with any through-hole T; however, the printed wiring board 2 of the present embodiment is provided with through-holes T for filling solder paste S at wiring end portions L to be connected to terminals 12 of the chip-type LEDs 1.

The number of chip-type LEDs 1 is adapted to be increased toward an outer circumference such that the chip-type LEDs 1 are substantially equally disposed on the printed wiring board 2.

Under such a configuration, the manufacturing method for the illumination device 100 according to the present embodiment is described.

First, in the printed wiring board 2, the through-holes T are provided at the wiring end portions L to be connected to the terminals 12 of each of the chip-type LEDs 1 (through-hole T forming step). This working step can be omitted by using the printed wiring board 2 of which the wiring end portions L are preliminarily provided with the through-holes T. In this embodiment, side surfaces of the through-holes T are adapted to be also covered with metal.

Figure 4:
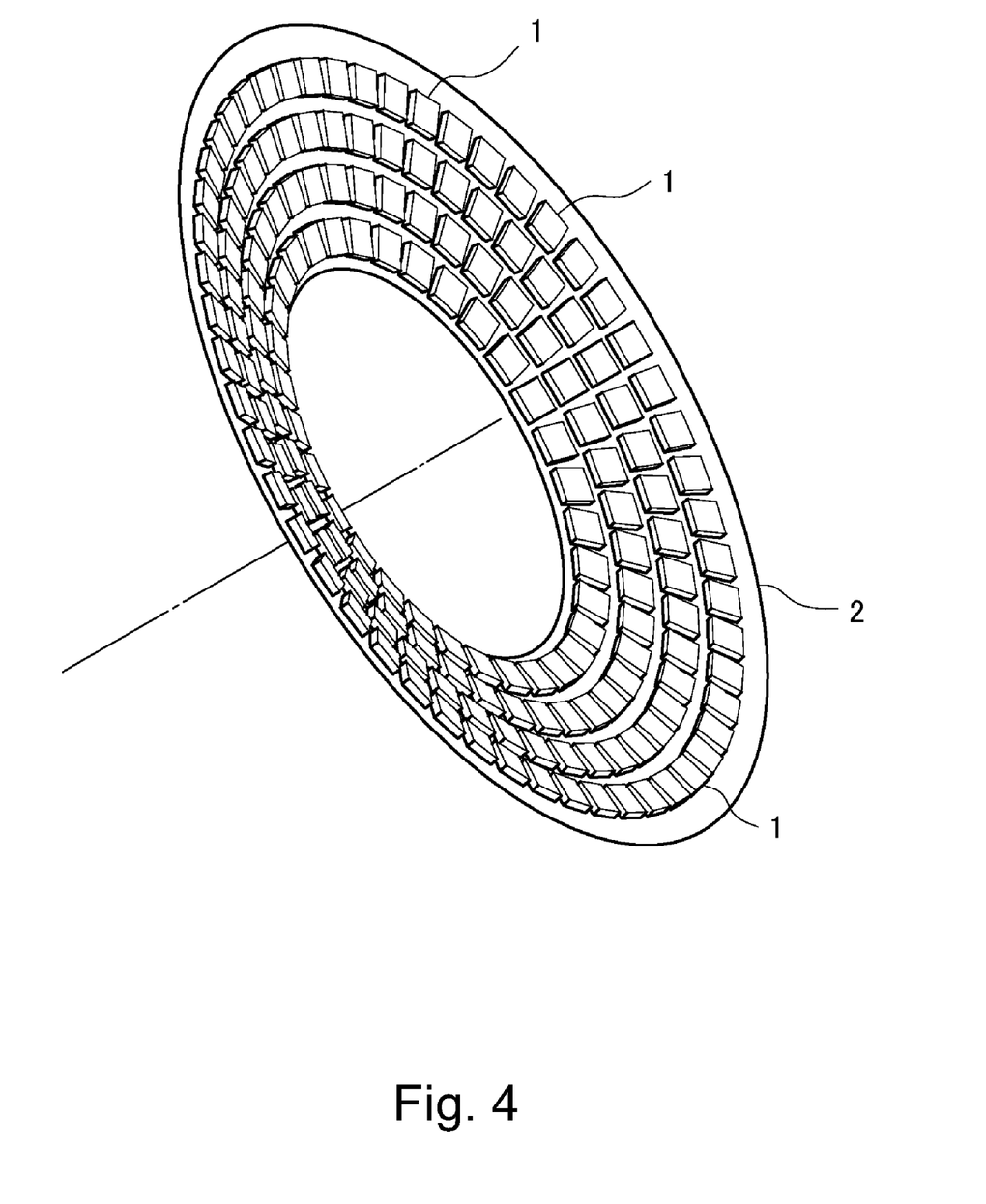
FIG. 4 is a schematic perspective view illustrating a state where the wiring board is rounded into a truncated conical shape.
Figure 5:
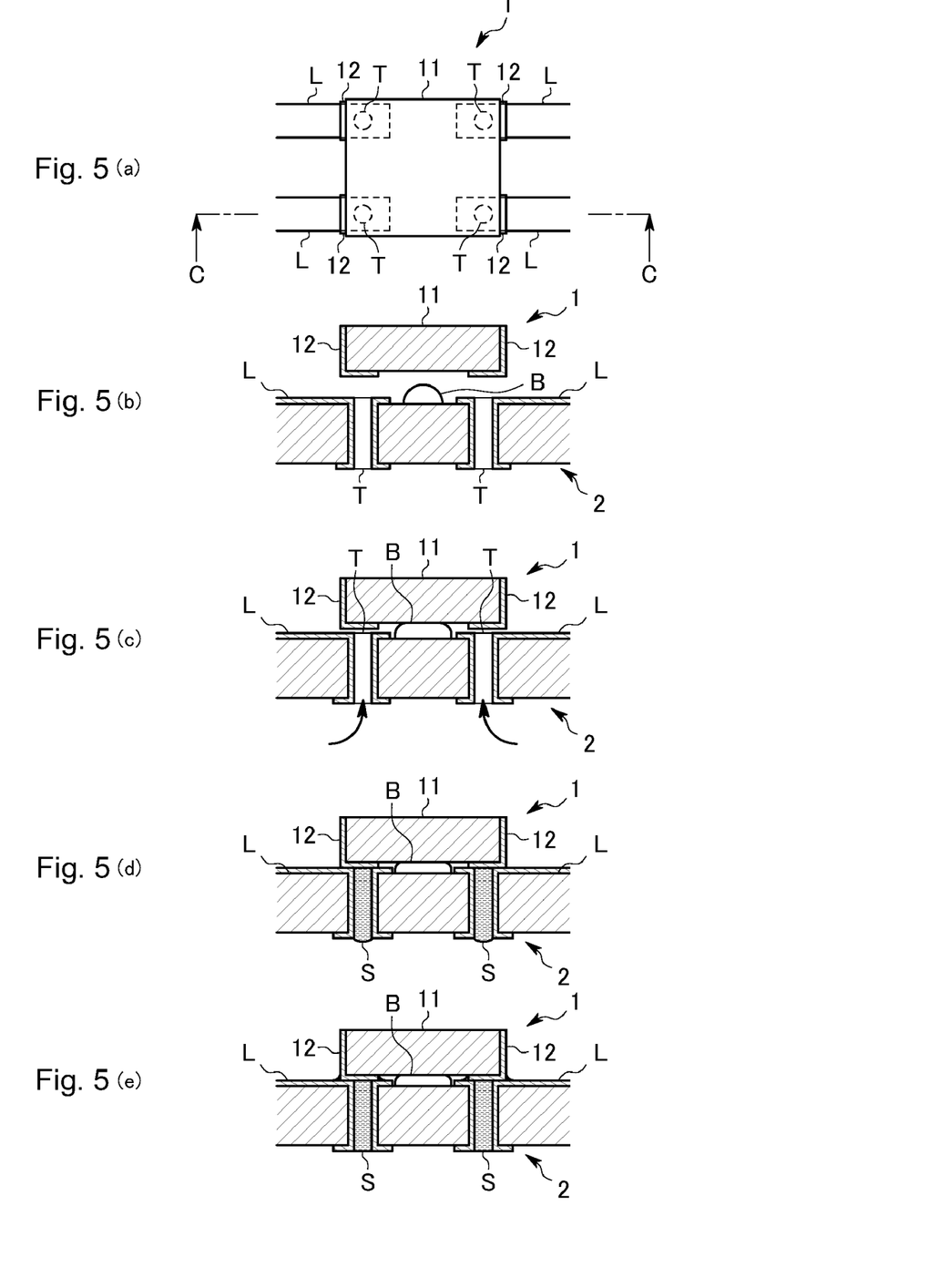

Then, a procedure for soldering the chip-type LEDs 1 onto the printed wiring board 2 already provided with the through-holes T is described referring to FIGS. 3 to 5.

FIGS. 5(a)-5(e) illustrate a work diagram that illustrates the soldering procedure with an enlarged chip-type LED 1. FIG. 5(a) is a diagram of the chip-type LED 1 as viewed from a top surface, and FIGS. 5(b), (c), (d), and (e) are diagrams illustrating respective working steps of the soldering procedure with use of a view of a C-C cross-section in FIG. 5(a).

As illustrated in FIG. 5(a), the chip-type LED 1 of the present embodiment is provided with two terminals 12 for each of both ends of an LED main body 11, i.e., four terminals 12 in total, and corresponding to each of the terminals 12, the print wiring board 2 is provided with a wiring line.

First, under the condition that the printed wiring board 2 is brought into a plate-like state as illustrated in FIG. 3, at positions where the LED main bodies 11 are desired to be temporarily fixed, bond B is placed with use of a method such as printing. As illustrated in FIG. 5(b), the chip-type LED 1 is temporarily fixed with a center of the LED main body 11 being placed on the bond B such that the respective terminals 12 correspond in position to the wiring end portions L. To specifically describe the temporary fixation of the chip-type LED 1 with the bond B, the bond-based fixation can hold the chip-type LED 1 more tightly than the paste-like solder to be described later, and even when the printed wiring board 2 is bent into a desired shape, the chip-type LED 1 does not fall. Also, the LED main body 11 is temporarily fixed only at one point, i.e., the center thereof, to prevent planar constraint from occurring, and the bond is adjusted to have a certain degree of viscosity, so that the bond-based fixation does not interfere even in the case of rounding the printed wiring board 2.

Subsequently, as illustrated in FIG. 5(c), from a back surface of the printed wiring board 2, i.e., from a surface on a side opposite to a surface on which the chip-type LED 1 is placed, the through-holes T are filled with the solder paste S (mounting step). The filling of the solder paste S is adapted to be performed by printing also from the back surface side. That is, separate printing is performed such that the surface is printed only with the bond B, and from the back surface, the through-holes T are filled with the solder paste S, and therefore trouble such as detachment of the bond B or the solder paste S by a printer during each of the working steps can be prevented.

As illustrated in FIG. 5(d), in a state where the through-holes T are sufficiently filled with the solder paste S, and the solder paste S is sufficiently distributed between the terminals 12 of the chip-type LED 1 and the wiring end portions L of the printed wiring board 2, the printed wiring board 2 is rounded and formed into the truncated conical shape as illustrated in FIG. 4 with the end edges of the printed wiring board 2 being brought into abutting contact with each other, and by grappling the grappling members 4 to each other, the shape is kept (rounding step).

By reflowing the printed wiring board 2 rounded into the truncated conical shape, the solder paste S is solidified to achieve soldering, and as illustrated in FIG. 5(e), the chip-type LED 1 is fixed onto the printed wiring board 2 (soldering step).

Finally, the rounded printed wiring board 2 is attached and fixed into the illumination case 3 to thereby complete the illumination device 100 as illustrated in FIG. 1.

According to the manufacturing method for the illumination device 100 of the present embodiment, the through-holes T that are essentially not required to be provided in the case of soldering the chip-type LED 1 of a surface mount type are provided at the wiring end portions L to temporarily fix the chip-type LED 1 with the bond B, and the solder paste S is used for the filling from the board back surface to thereby be able to prevent the trouble that the printed wiring board 2 cannot be rounded due to complete fixation of the chip-type LEDs 1 onto the printed wiring board 2 in the plate-like state.

Accordingly, although the chip-type LEDs 1 are used, the printed wiring board 2 can be easily formed into the truncated conical shape or another shape to manufacture the illumination device 100.

Also, the bond B and the solder paste S are configured to be applied or filled from the separate surfaces respectively, and therefore the detachment of the bond B or the solder paste S by machine contact during each of the working steps, or movement of the bond B or the solder paste S to another place can be prevented.

Further, in the state where the printed wiring board 2 is rounded, the solder paste S filled in the through-holes T can be reflowed to solder the chip-type LEDs 1 at one time, and therefore working efficiency is very high.

Next, a variation of the first embodiment is described.

In the first embodiment, the chip-type LEDs 1 are temporarily fixed with the bond B onto the printed wiring board 2 in the plate-like state, and then the through-holes T are filled with the solder paste S from the back surface; however, in an opposite manner, after the through-holes T have been filled with the solder paste S from the back surface, the chip-type LEDs 1 may be temporarily fixed with the bond B onto the printed wiring board 2. Even in the case of changing the order as described, the same effect as that in the first embodiment can be obtained.

Also, there may be employed a configuration in which after the chip-type LEDs 1 have been temporarily fixed with the bond B onto the printed wiring board 2 in the plate-like state (temporary fixing step), the printed wiring board 2 is rounded into the truncated conical shape (rounding step), and then the through-holes T are filled with the solder paste S from the back surface (filling step). Even in this case, before the printed wiring board 2 is rounded, the chip-type LEDs 1 are not completely soldered or fixed, so that the printed wiring board 2 can be easily rounded, and therefore the same effect as that in the first embodiment can be obtained.

Next, a second embodiment is described referring to FIGS. 3, 4, and 6. Note that members corresponding to those in the first embodiment are denoted by the same symbols.

In the second embodiment, as illustrated in FIG. 6(*a*), as a chip-type LED 1, one provided with one terminal 12 for each of both ends, i.e., two terminals 12 in total, is used. FIGS. 6(*b*), (*c*), (*d*), and (*e*) illustrate respective working steps of a soldering procedure in a D-D cross-section view in FIG. 6(*a*).

As illustrated in FIGS. 6(*a*)-6(*e*), in a printed wiring board 2 of the second embodiment, only one of a pair of wiring end portions L to be connected to the terminals 12 of the chip-type LED 1 is provided with a through-hole T (through-hole forming step). A site where the through-hole T is provided may be any one of the pair of wiring end portions L; however, considering manufacturing workability, it is better to provide the through-holes T with the sites being fixed to any one of the sides. On the assumption of such a printed wiring board 2, the soldering procedure is described below.

As illustrated in FIG. 6(*b*), only a wiring end portion L where the through-hole T is not provided on the printed wiring board 2 in a plate-like state is printed with first solder paste S1 that uses first solder S1 having a higher melting point than that of a second solder to be described later. The chip-type LED 1 is placed such that the terminals 12 of the chip-type LED 1 respectively correspond in position to the wiring end portions L.

Figure 6A:
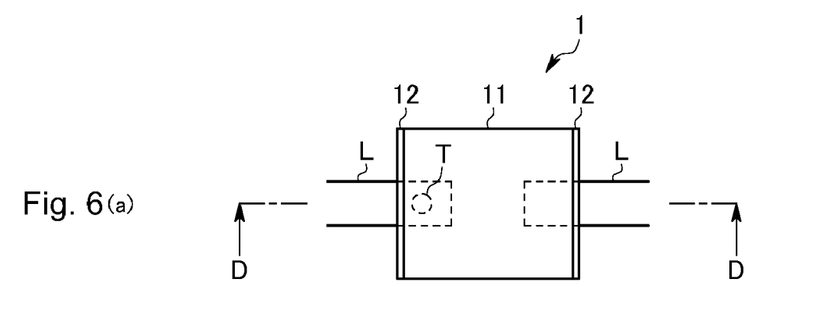
Figure 6B:
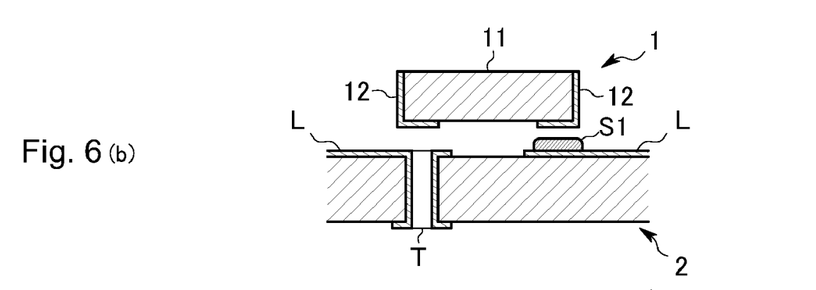
Figure 6C:
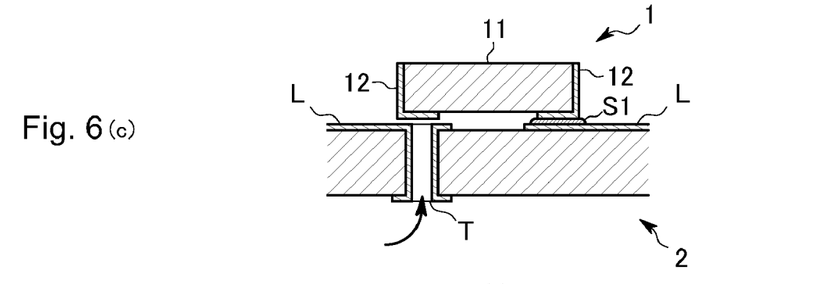
Figure 6D:
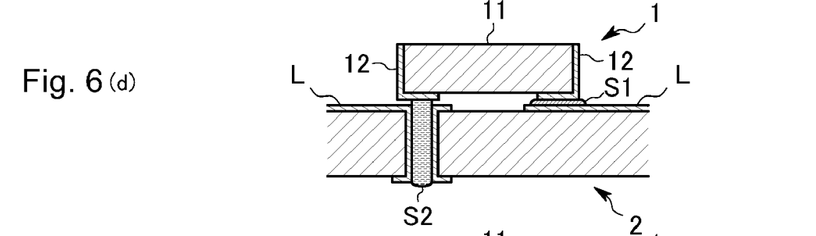
Figure 6E:
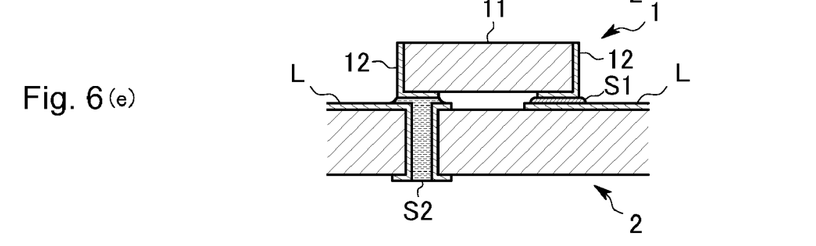

In a state where the respective LED chips 1 are placed with keeping the printed board in the plate-like state, reflow is performed to solidify the first solder S1.

As illustrated in FIG. 6(*c*), subsequently, to be able to solder a wiring end portion L where the through-hole T is provided and a terminal 12 of the chip-type LED 1 to each other, the through-hole T is filled with second solder paste S2 having a lower melting temperature than that of the first solder S1 (mounting step).

As illustrated in FIG. 6(*d*), when all of the through-holes T are filed with the second solder paste S2, the printed wiring board 2 is rounded into a truncated conical shape with end edges of the printed wiring board 2 being brought into abutting contact with each other (rounding step). At this time, soldering of the terminals 12 of the chip-type LED 1 is completed only to the wiring end portion L where the through-hole T is not provided, and therefore the chip-type LED 1 is fixed only with being in point contact. That is, the other terminal 12 is not fixed yet, and the chip-type LED 1 has a degree of freedom and is not fixed with being in line or plane contact, so that the printed wiring board 2 can be easily rounded.

The reflow is again performed at a lower temperature at which the first solder paste S1 is not melted, i.e., at a lower temperature than that of the melting point of the first solder S1, with keeping the state where the printed wiring board 2 is rounded into the truncated conical shape, and as illustrated in FIG. 6(*e*), the second solder paste S2 is solidified to complete all of the soldering steps (soldering step).

Finally, the printed board that has the LEDs 1 soldered to a surface and is rounded into the truncated conical shape as illustrated in FIG. 4 is attached into an illumination case 3 to thereby complete an illumination device 100.

As described, according to a manufacturing method as in the second embodiment, by using two types of the solder pastes S having the different melting temperatures without the temporary fixation with the bond B, the illumination device 100 can be manufactured with preventing the problem that the chip-type LEDs 1 are soldered onto the printed wiring board, and thereby the printed circuit board loses the flexibility to be rounded.

Also, a reason to produce such an effect is because a new method is employed in which, in the case of soldering the chip-type LEDs 1, the through-holes T at the wiring end portions L are formed, which are usually not provided in the printed wiring board 2, and then filled with the solder paste S from the back surface.

Next, a variation of the second embodiment is described.

Even in the second embodiment, before the soldering with the first solder, the through-holes T may be filled with the second solder. In such a case, as the second solder paste S2, one having a higher melting point than that of the first solder paste S1 is used.

Also, the soldering with the first or second solder may be performed not by the reflow but by manual working.

Even in the variation as described above, almost the same effect as that in the second embodiment can be obtained.

Other variations are described.

In each of the first and second embodiments, the illumination device using the printed wiring board having the truncated conical shape into which the partially ring-shaped printed wiring board having the cutout is used and rounded is described; however, the printed wiring board may be linear. In this case, an illumination device having a cylindrically shaped light emitting part that is formed when the linear printed wiring board is rounded can be manufactured.

There may be employed a configuration in which, by variously changing the partial ring shape, rounding into a truncated conical shape other than that illustrated in the drawings can be performed.

In the case where the number of sites at which the LED is fixed onto the printed wiring board is two, the fixation should be performed at both of the two sites with conductive paint (solder); however, in the case where the number of fixing sites is three or more, all of the three sites are not necessarily applied with the conductive paint (at least two sites (two poles) are required for applying current). That is, in the case where the number of fixing sites is three or more, at least two sites are applied with the conductive paint, and the rest of the sites may be applied with any paint (any of conductive and insulating paints can be applied). In other words, in the case of temporarily or permanently fixing the LED onto the printed wiring board, if at least the LED is adapted to be applied with current to emit light, all of the fixing sites are not required to be applied with the conductive paste.

In addition, the respective embodiments may be appropriately combined, or various modifications may be made without departing from the spirit of the present invention.

REFERENCE SIGNS LIST

100: Illumination device
1: Chip-type LED
12: Wiring board
L: Wiring end portion
T: Through-hole
S: Solder paste
S1: First solder
S2: Second solder
B: Bond

The invention claimed is:

1. A method for manufacturing an illumination device in which a chip-type LED is mounted on a flexible strip-like wiring board having a partial ring shape or a linear shape, and the wiring board is rounded into a truncated conical shape or a cylindrical shape with end edges of the wiring board being brought into abutting contact with each other, the method having:
a through-hole forming step of, in the wiring board, providing a through-hole for filling solder paste at a wiring end portion to be connected with a terminal of the LED;
a mounting step of temporarily fixing the LED with bond onto the wiring board in a plate-like state, and filling the through-hole with the solder paste from a back surface of the wiring board;
a rounding step of rounding the wiring board into the truncated conical shape or the cylindrical shape, the wiring board being mounted with the LED in the mounting step and having the through hole filled with the solder paste; and
a soldering step of reflowing the wiring board in a rounded state.

2. A method for manufacturing an illumination device in which a chip-type LED is mounted on a flexible strip-like wiring board having a partial ring shape or a linear shape, and the wiring board is rounded into a truncated conical shape or a cylindrical shape with end edges of the wiring board being brought into abutting contact with each other, the method having:
a through-hole forming step of, in the wiring board, providing a through-hole for filling solder paste at a wiring end portion to be connected with a terminal of the LED;
a temporary fixing step of temporarily fixing the LED with bond onto a surface of the wiring board in a plate-like state;
a rounding step of rounding the wiring board into the truncated conical shape or the cylindrical shape, the wiring board being mounted on the surface with the LED by the temporary fixing step;
a filling step of filling the through hole with the solder paste from a back surface of the wiring board in a rounded state; and
a soldering step of reflowing the wiring board in the rounded state, the wiring board having the through-hole filled with the solder paste.

3. A method for manufacturing an illumination device in which a chip-type LED is mounted on a surface of a flexible strip-like wiring board having a partial ring shape or a linear shape, and the wiring board is rounded into a truncated conical shape or a cylindrical shape with end edges of the wiring board being brought into abutting contact with each other, the method having:
a through-hole forming step of, in the wiring board, providing a through-hole for filling with solder paste at a part of a wiring end portion to be connected with a terminal of the LED;
a mounting step of bringing the wiring board into a plate-like state, soldering a wiring end portion other than the wiring end portion where the through-hole for filling with the solder paste is formed and a terminal of the LED to each other with first solder, and filling the through-hole with paste-like second solder that is melted at a lower temperature than that of the first solder;
a rounding step of rounding the wiring board into the truncated conical shape or the cylindrical shape, the wiring board being mounted with the LED in the mounting step and having the through-hole filled with the paste-like second solder; and
a soldering step of reflowing the wiring board in a rounded state at a temperature at which the first solder is not melted but the second solder is melted.

4. A method for manufacturing an illumination device in which a chip type LED is mounted on a surface of a flexible strip-like wiring board having a partial ring shape or a linear shape, and the wiring board is rounded into a truncated conical shape or a cylindrical shape with end edges of the wiring board being brought into abutting contact with each other, the method having:
a through-hole forming step of, in the wiring board, providing a through-hole for filling with solder paste at a part of a wiring end portion to be connected with a terminal of the LED;
a mounting step of bringing the wiring board into a plate-like state, soldering with first solder a wiring end portion other than the wiring end portion where the through-hole for filling with the solder paste is formed and a terminal of the LED to each other, and filling the through-hole with paste-like second solder;
a rounding step of rounding the wiring board into the truncated conical shape or the cylindrical shape, the wiring board being mounted with the LED in the mounting step and having the through-hole filled with the paste-like second solder; and
a soldering step of, in the wiring board in a rounded state, providing heat from a back surface of the through-hole to melt the second solder.

5. The method for manufacturing an illumination device according to claim 4, wherein
in the mounting step, paste-like first solder is used to perform soldering by reflow.

6. An illumination device in which a chip-type LED is mounted on a surface of a flexible strip-like wiring board having a partial ring shape or a linear shape, and the wiring board is rounded into a truncated conical shape or a cylindrical shape with end edges of the wiring board being brought into abutting contact with each other, the illumination device being formed by:
in the wiring board, providing a through-hole for filling with solder paste at a wiring end portion to be connected with a terminal of the LED;
temporarily fixing the LED with bond onto the wiring board held in a plate-like state, and filling the through-hole with the solder paste from a back surface of the wiring board; and
rounding the wiring board into the truncated conical shape or the cylindrical shape, the wiring board being mounted with the LED and having the through hole filled with the solder paste, and reflowing the wiring board in a rounded state to solder the LED.

7. An illumination device in which a chip-type LED is mounted on a surface of a flexible strip-like wiring board having a partial ring shape or a linear shape, and the wiring board is rounded into a truncated conical shape or a cylindrical shape with end edges of the wiring board being brought into abutting contact with each other, the illumination device being formed by:

in the wiring board, providing a through-hole for filling with solder paste at a part of a wiring end portion to be connected with a terminal of the LED;

bringing the wiring board into a plate-like state, soldering with first solder a wiring end portion other than the wiring end portion where the through-hole for filling with the solder paste is formed and a terminal of the LED to each other, and filling the through-hole with paste-like second solder that is melted at a lower temperature than that of the first solder; and rounding the wiring board into the truncated conical shape or the cylindrical shape, the wiring board being mounted with the LED in the mounting step and having the through-hole filled with the paste-like second solder, and reflowing the wiring board in a rounded state at a temperature at which the first solder is not melted but the second solder is melted.

8. The method for manufacturing an illumination device according to claim 3, wherein in the mounting step, paste-like first solder is used to perform soldering by reflow.

* * * * *